United States Patent [19]

Wittrock

[11] Patent Number: 5,344,017
[45] Date of Patent: Sep. 6, 1994

[54] INSTRUMENT POUCH WITH IN-POUCH STERILE PROCESSING INDICATOR

[76] Inventor: Paul M. Wittrock, 1545 Flowerdale St., Simi Valley, Calif. 93063

[21] Appl. No.: 106,213

[22] Filed: Aug. 13, 1993

[51] Int. Cl.⁵ .............................................. B65D 73/00
[52] U.S. Cl. .................................. 206/459.1; 206/363; 206/439
[58] Field of Search ............. 206/363, 438, 439, 459.1

[56] References Cited

U.S. PATENT DOCUMENTS

| | | | |
|---|---|---|---|
| 3,246,959 | 4/1966 | Brewer | 206/439 |
| 3,258,312 | 6/1966 | Olsen | 206/459.1 |
| 3,460,742 | 8/1969 | Langdon | 206/439 |
| 3,627,611 | 12/1971 | Bonk | 206/363 |
| 3,704,096 | 11/1972 | Verses et al. | 206/459.1 |
| 3,768,725 | 10/1973 | Pilaro | 206/439 |
| 3,991,881 | 11/1976 | Augurt | 206/439 |
| 4,091,921 | 5/1978 | Lewis | 206/363 |
| 4,098,577 | 7/1978 | Halpern | 206/459.1 |
| 4,121,714 | 10/1978 | Daly et al. | 206/459.1 |
| 4,168,779 | 9/1979 | Yokokoji et al. | 206/439 |
| 4,206,844 | 6/1980 | Thuramoto et al. | 206/459.1 |

*Primary Examiner*—David T. Fidei
*Attorney, Agent, or Firm*—Louis J. Bachand

[57] ABSTRACT

A medical instrument sterilization processing pouch is provided having a sterile processing indicator protected between the walls forming the pouch to register sterilizing processing of the medical instruments.

12 Claims, 2 Drawing Sheets

INSTRUMENT POUCH WITH IN-POUCH STERILE PROCESSING INDICATOR

TECHNICAL FIELD

This invention has to do with effective maintenance of cross-contamination control in dental, medical and veterinary operatories, and more particularly with improved temporary packaging for sterile-processed instruments, in-pouch sterile processing of such instruments in improved packaging, and with sterile instrument packaging pouches having sterile processing indicators within the pouch sealed volume for monitoring subjection of contained instruments to sterile processing.

BACKGROUND

Increased emphasis has been placed on the sterilization of medical instruments between uses on different patients. In dental offices for example, instruments are gathered after use, cleaned, packaged in sterilizable pouches, sealed in a closed volume defined by the pouch walls, and then subjected to a sterilizing environment such as an autoclave wherein steam or high temperature water vapor is used to sterilize process the instruments. Alternatively, the pouch-enclosed instruments are subjected to a sterilizing gas such as ethylene oxide. The instruments are then stored in the sealed pouches for later use. To ensure that a given pouch has been subjected to the sterilization procedures, indicators are used. These typically are printing inks having color change response to steam, high temperature water vapor or a sterilizing gas such as ethylene oxide, or other sterilizing agent, e.g. the ink permanently changes from gray to brown when exposed to sterilizing conditions.

Typical sterilizing pouches are formed of sheet materials printed with identifying brand names and other information on an outward face, and it has been the practice to place the indicator ink on this same face. This practice has several drawbacks, including lack of protection for the ink from frictional removal during handling and storage, and remoteness of the ink to the instruments being sterile processed, whereby the ink may record a sterilizing exposure but the instruments have not actually received the exposure, only the ink has.

SUMMARY OF THE INVENTION

It is an object therefore of the present invention to provide an improved sterilization and storage pouch for medical instruments. It is another object to provide such a pouch having an indicator ink thereon protected from frictional removal during handling and storage of the pouch. It is another object to provide such a pouch wherein the medical instruments and the indicator ink are within the same sealed volume during sterilization processing. It is yet another object to provide such a pouch wherein only exposure of the medical instruments to sterilizing processing is recorded by the indicator ink.

Sterile-processing and cognitives thereof refers to the subjection of medical, dental, veterinary and like instruments to instruments closed within a controlled environment to gases, radiation and/or vapors able to penetrate the closed environment and to sterilize the instruments within. In the invention there is no limitation as to the sterilizing agent, or the material defining the enclosure, or the indicator used to verify the sterile-processing event.

The foregoing and other objects to become apparent hereinafter are realized in accordance with the invention in a medical instrument sterilization processing pouch within which medical instruments are sealed and sterile-processed and stored for later use, and wherein within the sealed pouch there is located a sterile-processing indicator having signal response to sterile processing conditions experienced by said instruments.

In this and like embodiments, the sterile-processing indicator comprises an ink having color-change response to exposure to sterilization processing to signal a history of sterile processing, the ink is responsive to sterilizing steam or vapor, or organic agents such as formaldehyde, or the ink is responsive to exposure to radiation or a sterilizing gas, e.g. ethylene oxide. The sterile-processing indicator may have separate portions separately responsive to different pairs of sterilizing agents, e.g. sterilizing steam or vapor and sterilizing gas.

In further embodiments, the pouch comprises first and second sheet material walls, the walls being joined to define the pouch, one of the sheet material walls is transparent and water vapor impervious, and one of said walls is cellulosic and water vapor and sterilization gas pervious, and the joinder of the walls defines a perimetrical seal about a partially closed volume within which the instruments are placed for sterilization, the pouch having also a flap on one of the walls arranged to overlie the other of the walls in sealed relation to fully enclose the volume.

In a highly preferred embodiment, the sterile processing indicator is within the enclosed volume, the sterile processing indicator is adjacent the perimetrical seal, and there is further included means blocking frictional contact between the sterile processing indicator and instruments within the enclosed volume.

In this and like embodiments, the blocking means typically comprises sealed or partly sealed together portions of the sheet material walls inward of the perimetrical seal and arranged laterally adjacent the sterile processing indicator to block frictional contact between the sterile processing indicator and medical instruments within the volume.

In another embodiment, the invention provides a medical instrument sterilization processing pouch comprising first and second generally planar walls, the walls being sealed together to define a perimetrically sealed volume within which medical instruments are sterile-processed and stored for later use, and a sterile-processing indicator having signal response to sterile processing conditions, the indicator being located between the walls and arranged to signal a history of pouch exposure to sterile processing conditions.

In this and like embodiments, the first wall comprises cellulosic sheet material, the sterile processing indicator being printed on the inward face thereof, the second wall overlies the first wall inward face, in protective relation over the indicator, and the second wall comprises sheet material through which the sterile processing indicator is visible, the sterile processing indicator is printed on the first sheet within the sealed volume and is visible through the second sheet, and there is further provided means blocking frictional contact between the sterile processing indicator and instruments within the sealed volume, the blocking means comprising sealed together portions of the sheet material walls arranged laterally adjacent the sterile processing indicator to block frictional contact between the sterile processing indicator and medical instruments within the sealed volume.

BRIEF DESCRIPTION OF THE DRAWINGS

The invention will be further described as to an illustrative embodiment in conjunction with the attached drawings in which.

DETAILED DESCRIPTION

Figure 1:
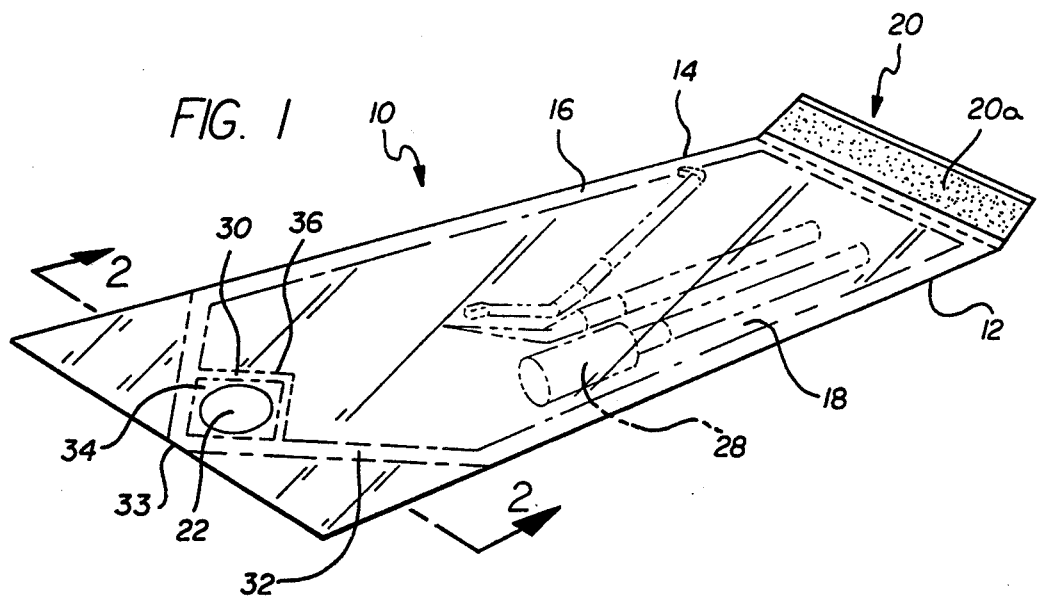
FIG. 1 is a perspective view of the invention pouch.
Figure 2:
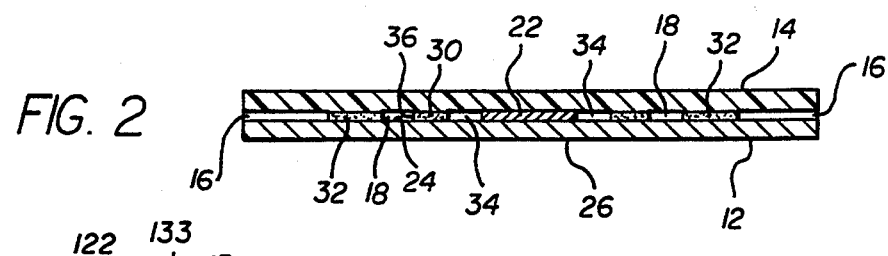
FIG. 2 is a sectional view thereof taken on line 2—2 in FIG. 1.

With reference now to the drawings in detail, in FIGS. 1 and 2 pouch 10 is shown to comprise a first or lower sheet 12, typically planar sheet material, suitably cellulosic in composition and printable, and pervious to steam, water vapor and sterilization gases. A second, upper sheet 14 is provided, also planar, but typically of transparent plastic such as polyester, or polyester/polyolefin laminate, impervious to water vapor, steam and typical sterilizing gases overlies the first sheet and is heat sealed thereto along a perimeter seal line 16, to form the pouch 10 and the pouch enclosed or sealed volume 18. Perimetrical seal line 16 runs around three sides of the volume 18. The remaining side, adjacent the lower end of the pouch 10, is closed by folding over the flap 20 of the lower sheet 12, as shown, the flap having contact adhesive 20a thereon so as to seal to the upper sheet 14 and complete the sealing of volume 18.

Thusfar described the pouch is conventional. Unlike previously known medical instrument sterilization pouches, however, the present pouch 10 has a specially placed sterilization indicator, indicator ink dot 22, between the sheets 12 and 14, printed on the inner face 24 of the lower sheet 12, rather than on the outer face 26 of the lower sheet 12 as has been the common practice. The special placement protects the indicator from tribological removal, and, importantly, when placed in the pouch 10 with the medical instruments 28 reveals the sterilization exposure of the instruments and not merely the exposure of outer wall of the pouch to sterilization processing.

That is, having indicator ink dot 22 within the perimetrical seal line 16, ensures that it is exposed only to sterilization conditions within that line, just as the instruments 28 themselves within the volume 18 are only just so exposed. This provides a more accurate monitoring of sterilization condition exposure than the same ink dot on the outside of the pouch, as has been conventional.

The sterilization indicator dot 22 is a typical shape, but no particular shape is required, and linear, square, arrow-shaped, and even legible indicia may be formed of the indicator ink in lieu of the dot shape shown. The inks used to print the dot 22 are conventional in the industry for monitoring sterilization exposure to such divers sterilants as autoclave steam, dry heat, ethylene oxide gas, formaldehyde gas, hydrogen peroxide gas and radiation and other inorganic and organic agents suitable for such purposes. Commercial indicator products that may be used include such products as Tempilinks ® available from Tempil Division of Big Three Industries, Inc., South Plainfield, NJ. Use of inks giving a substantial color change on exposure to steam, water vapor, organic agent such as formaldehyde, radiation, or a gas such as ethylene oxide exposure and/or other agents mentioned are preferred.

The sterilization indicator dot 22 may be located anywhere within the volume 18, and is desirably protected from deleterious frictional contact with the medical instruments 28. Toward this end, a protective barrier 30 is preferably provided between the dot 22 and the medical instruments 28, by sealing the upper and lower walls in a secondary location to form a blocking seal 32 between the dot and the major portion of the sealed volume 18 wherein the instruments are likely to reside. The barrier 30 may be located along the side of the volume 18, be integrated into the seal line 16, as shown in FIG. 1, by bifurcating the seal line at the apex 33 thereof to form a diamond-shaped enclosure 34 within which the indicator ink dot 22 is placed. The inner portion 36 of the seal line 16 forming barrier 30 is desirably discontinuous to integrate the atmosphere of the main portion of the sealed volume 18 with the interior of the enclosure 34, thus maintaining commonality of sterilizing processing exposure between the indicator dot 22 and the medical instruments 28.

In the following description, like parts to FIGS. 1 and 2 are given like numbers with the addition of 100, 200 or 300.

Figure 3:
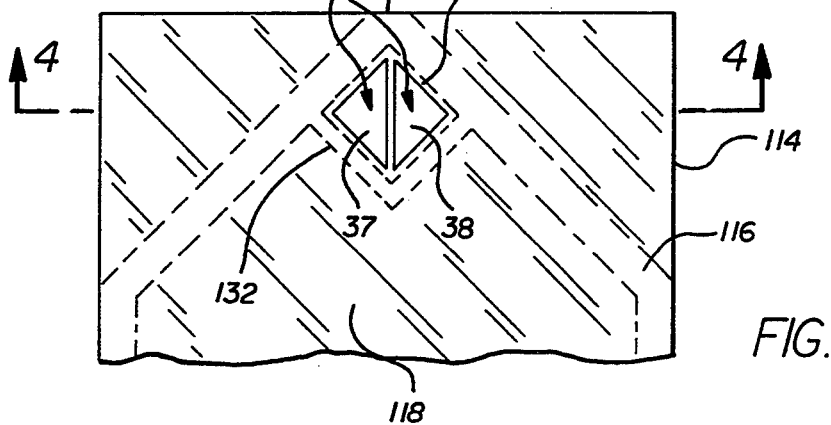
FIG. 3 is a fragmentary plan view of another form of the invention.
Figure 4:
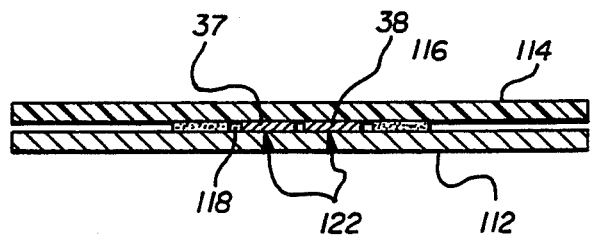
FIG. 4 is a sectional view thereof taken on line 4—4 in FIG. 3.

In FIGS. 3 and 4, an alternate form of the invention is shown to comprise pouch 110 wherein two indicator inks are printed within the enclosure 134 to define a divided dot 122 having the shape of opposed triangular portions 37, 38. This form of the invention enables monitoring two different sterilization processing routines, as each portion 37, 38 is responsive to a different sterilant, e.g. portion 37 is responsive to steam or heated water vapor, and portion 38 is responsive to a gas such as ethylene oxide.

Figure 5:
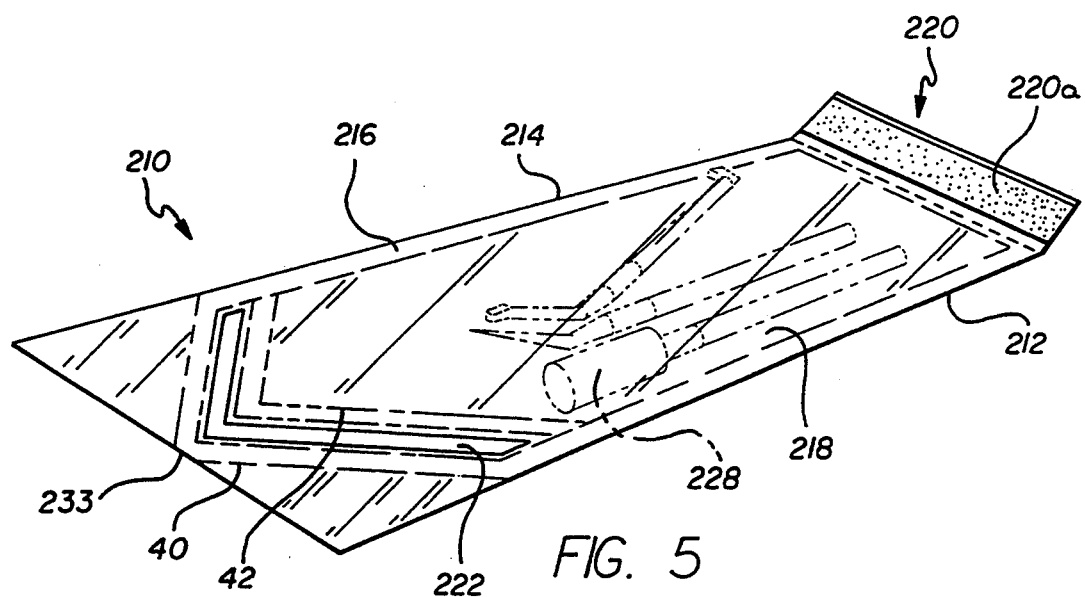
FIG. 5 is a view like FIG. 1 of another embodiment of the invention.

In FIG. 5, pouch 210 has seal line 216, which at its apex 233 is divided in chevron fashion into inner and outer lines 40, 42, with the indicator ink being printed as a bead 222 between the inner and outer seal line segments, affording protection to the dots and intimate contact with the sterilization condition within the sealed volume 218.

Figure 6:
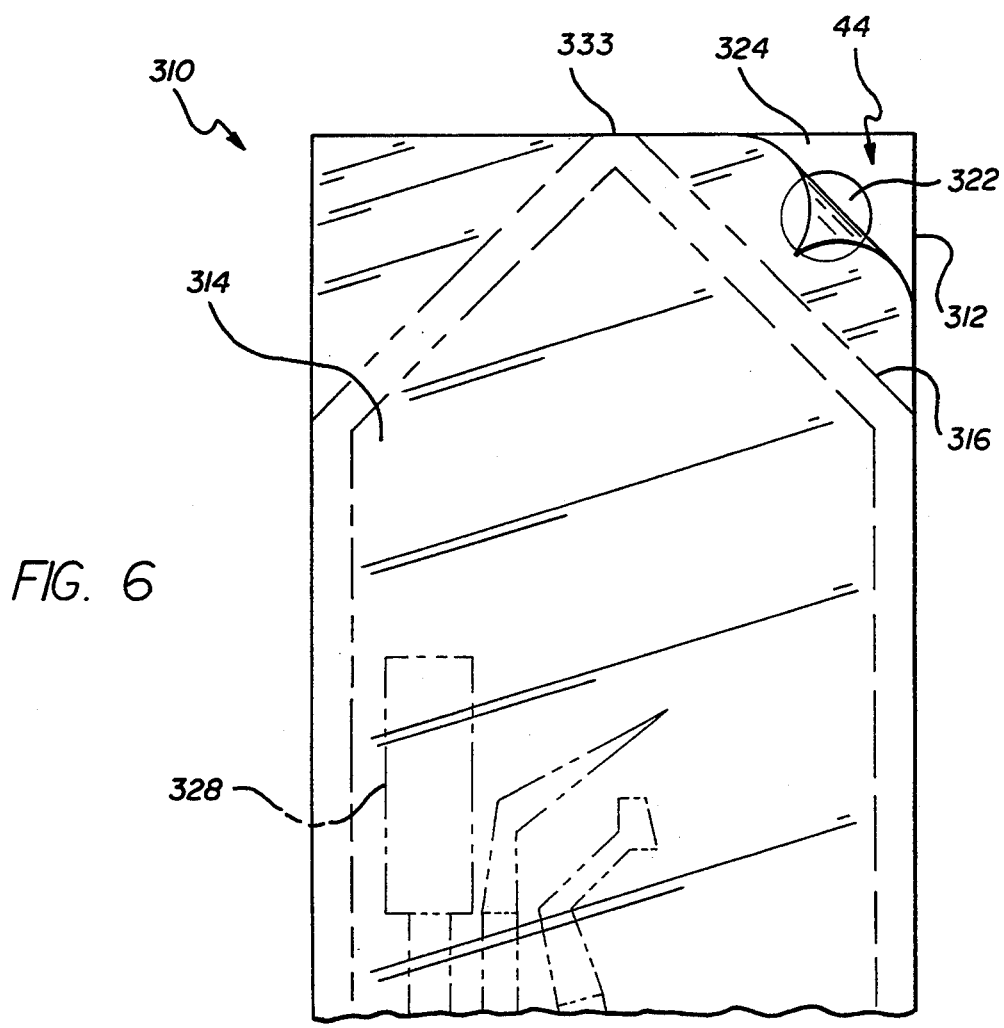
FIG. 6 is a view like FIG. 3 of another form of the invention.

In FIG. 6, pouch 310 has indicator dot 322 placed on the corner 44 of the inner face 324 of lower sheet material 312, just outside the seal line 316, to be visible under the flap 46 of the upper sheet 314 and protected thereby in the use condition of the pouch 310.

The present invention thus provides an improved sterilization and storage pouch for medical instruments having an indicator ink thereon protected from frictional removal during handling and storage of the pouch, and wherein the medical instruments and the indicator ink are within the same sealed volume during sterilization processing, whereby only a history of exposure of the medical instruments to sterilizing processing is recorded by the indicator ink.

I claim:

1. Medical instrument sterilization processing pouch comprising first and second sheet material walls joined by a perimetrical seal to have a closed volume within which medial instruments are sealed and sterile-processed and stored for later use, said perimetrical seal being tapered at one end of said pouch to limit locally the area of seal between said sheet material walls for ease of separating said sheet material walls and opening said seal, and within said pouch closed volume a sterile-processing indicator having signal response to sterile processing conditions experienced by said instruments, said sterile processing indicator being enclosed within said closed volume by additional seal lines of relatively less width than said perimetrical seal and extending at right angles to the tapered portions of said perimetrical seal to form a diamond shaped enclosure for said sterile processing indicator to limit the increase in seal area forming said sterile processing indicator enclosure.

2. Pouch according to claim 1, in which said sterile processing indicator comprises an ink having color-change response to exposure to sterilization processing to signal a history of sterile processing.

3. Pouch according to claim 2, in which said ink is responsive to sterilizing steam or vapor.

4. Pouch according to claim 2, in which said ink is responsive to exposure to a sterilizing gas, organic agent or radiation.

5. Pouch according to claim 4, in which said sterilizing gas comprises ethylene oxide.

6. Pouch according to claim 1, in which said sterile-processing indicator has separate portions separately responsive to sterilizing steam or vapor, sterilizing gas, organic agent or radiation.

7. Pouch according to claim 1, including also a flap on one of said walls arranged to overlie the other of said walls in sealed relation to fully enclose said closed volume.

8. Pouch according to claim 7, in which said sterile processing indicator is within said enclosed volume.

9. Pouch according to claim 8, in which said sterile processing indicator is adjacent said perimetrical seal.

10. Pouch according to claim 8, in which said diamond shaped enclosure blocks frictional contact between said sterile processing indicator and instruments within said closed volume.

11. Pouch according to claim 10, in which said diamond shaped enclosure is partly formed by said tapered portions of said perimetrical seal.

12. Pouch according to claim 1, in which said sterile processing indicator is beyond the tapered portion of said perimetrical seal and covered between said first and second sheet materials.

* * * * *